(12) United States Patent
Li

(10) Patent No.: US 10,913,894 B1
(45) Date of Patent: Feb. 9, 2021

(54) CONSTRUCTION METHOD FOR ECOLOGICALLY PROTECTING EXPANSIVE SOIL SLOPE BY COMBINING PHOSPHOGYPSUM WITH MICROBIAL MINERALIZATION

(71) Applicant: Institute of Geology and Geophysics, Chinese Academy of Sciences, Beijing (CN)

(72) Inventor: Zhiqing Li, Beijing (CN)

(73) Assignee: INSTITUTE OF GEOLOGY AND GEOPHYSICS, CHINESE ACADEMY OF SCIENCES

( * ) Notice: Subject to any disclaimer, the term of this patent is extended or adjusted under 35 U.S.C. 154(b) by 0 days.

(21) Appl. No.: 16/914,251

(22) Filed: Jun. 26, 2020

(30) Foreign Application Priority Data

Apr. 20, 2020 (CN) .......................... 2020 1 0313315

(51) Int. Cl.
| | |
|---|---|
| *C09K 17/06* | (2006.01) |
| *C12N 1/20* | (2006.01) |
| *E02D 17/20* | (2006.01) |
| *C09K 17/10* | (2006.01) |
| *E02D 17/18* | (2006.01) |
| *E02D 3/00* | (2006.01) |

(52) U.S. Cl.
CPC .............. *C09K 17/06* (2013.01); *C09K 17/10* (2013.01); *C12N 1/20* (2013.01); *E02D 3/005* (2013.01); *E02D 17/18* (2013.01); *E02D 17/20* (2013.01); *C12N 2500/05* (2013.01); *E02D 2300/0076* (2013.01)

(58) Field of Classification Search
CPC .......... C09K 17/06; C09K 17/10; C12N 1/20; C12N 2500/05; E02D 3/05; E02D 17/18; E02D 17/20
See application file for complete search history.

(56) References Cited

U.S. PATENT DOCUMENTS

| | | | |
|---|---|---|---|
| 4,448,566 A * | 5/1984 | King ...................... E01C 3/003 | 264/34 |
| 2009/0050025 A1* | 2/2009 | Wissa et al. .............. E02B 3/10 | 106/786 |
| 2012/0275861 A1* | 11/2012 | Myslowski et al. .... E01C 7/267 | 404/75 |

FOREIGN PATENT DOCUMENTS

CN 109824335 A * 5/2019

* cited by examiner

*Primary Examiner* — Tara Mayo-Pinnock
(74) *Attorney, Agent, or Firm* — Mark C. Johnson; Johnson Dalal

(57) ABSTRACT

The present invention provides a construction method for ecologically protecting an expansive soil slope by combining phosphogypsum with microbial mineralization. The method includes: (1) placing *Bacillus pasteurii* in a culture medium to prepare a microbial solution, and mixing urea, calcium chloride and water to prepare a cementing solution; (2) preparing a mixture with phosphogypsum fly ash and soil; mixing the mixture, the microbial solution and water well, and adding the cementing solution and water to prepare an improving mixture slurry; and (3) spraying the improving mixture slurry to a face of the slope by wet spraying, and covering with a non-woven fabric by tying and fixing.

1 Claim, 2 Drawing Sheets

CONSTRUCTION METHOD FOR ECOLOGICALLY PROTECTING EXPANSIVE SOIL SLOPE BY COMBINING PHOSPHOGYPSUM WITH MICROBIAL MINERALIZATION

TECHNICAL FIELD

The present invention relates to the field of slope engineering, and in particular to a construction method for ecologically protecting an expansive soil slope by combining phosphogypsum with microbial mineralization.

BACKGROUND

Expansive soil contains rich clay minerals such as montmorillonite and illite, and has the characteristics of swelling with water and shrinking with water loss. Due to the weak erosion resistance of the expansive soil, the excavation of slopes during rains is prone to gradual cracking, resulting in the landslide of the expansive soil slopes. The conventional slope protection methods include arched slope protection, grid beam slope protection, mortar rubble slope protection and other engineering measures. These methods have high cost, and their gray protection design is inharmonious with the surrounding landscape, and easy to cause secondary collapse.

Phosphogypsum is a byproduct produced in the production of phosphoric acid with apatite and sulfuric acid by wet process in chemical plants. The production of 1 ton of phosphoric acid yields about 5 tons of phosphogypsum. Phosphogypsum is a powdery material with little plasticity. It is slightly acidic due to the residual phosphoric acid, sulfuric acid and hydrofluoric acid. In addition, phosphogypsum is rich in available phosphorus, which can be used for plant growth. China produces more than 8 million tons of phosphogypsum every year. By the end of 2011, China had overstocked more than 300 million tons of phosphogypsum. If the phosphogypsum is applied to engineering design through technical measures, the overstocked phosphogypsum will be greatly reduced. This will save the land resources, avoid the collapse of phosphogypsum dams, and turn waste into treasure to give play to the benefits of phosphogypsum The soil contains a large number of microbes, and functional microbes can be selected and cultured for slope protection, which can cement soil particles, resist rain erosion, and promote plant growth. The addition of microbes is conducive to harmonize the slope protection with the surrounding ecological environment.

SUMMARY

An objective of the present invention is to provide a construction method for ecologically protecting an expansive soil slope by combining phosphogypsum with microbial mineralization. The present invention prevents a shallow landslide of the expansive soil slope, and reduces the stock of solid phosphogypsum waste, thereby saving the land resources and harmonizing with the surrounding ecological environment.

The present invention adopts the following technical solution: a construction method for ecologically protecting an expansive soil slope by combining phosphogypsum with microbial mineralization, including the following steps:

(1) preparing a culture medium and a microbial solution, where a mixed solute in the culture medium includes bean pulp, $(NH_4)_2SO_4$, $Na_2HPO_4$ and NaOH: weighing 40 parts of bean pulp, 10 parts of $(NH_4)_2SO_4$, 3.55 parts of $Na_2HPO_4$ and 40 parts of NaOH by mass to prepare the mixed solute of the culture medium; mixing the mixed solute of the culture medium with water to prepare a liquid medium, the content of the bean pulp in the liquid medium being controlled at 20-60 g/L; sealing and sterilizing the liquid medium in an autoclave at 121° C. for 25 min, and then cooling to 30±2° C. for use; adding 1 part by volume of *Bacillus pasteurii* solution to 100 parts by volume of liquid medium to prepare the microbial solution; placing the microbial solution into a constant-temperature shaking incubator at 30° C., and shaking at 200 rpm for more than 24 h until an optical density of the *Bacillus pasteurii* in the microbial solution at a wavelength of 600 nm ($OD_{600}$) is 1.5±0.2;

(2) preparing a cementing solution, where a mixed solute in the cementing solution includes urea and calcium chloride: weighing 2 parts of granular urea and 1 part of powdered calcium chloride by mass to prepare the mixed solute, and mixing the mixed solute with water to prepare the cementing solution with a concentration of 0.5±0.1 mol;

(3) preparing a mixture including phosphogypsum, fly ash and soil: weighing 19 parts of phosphogypsum, 1 part of fly ash and 40-50 parts of soil by dry mass, and mixing well to obtain the mixture, where the soil in the mixture is expansive soil, cohesive soil, silt, loam or planting soil;

(4) preparing an improving mixture slurry: weighing 100-1,000 parts of mixture, 1 part of microbial solution and 10 parts of cementing solution by volume; first mixing the 100-1,000 parts of mixture and 1 part of microbial solution with water well, where the water is added until a moisture content of the soil in the mixture reaches a liquid limit; then adding the 10 parts of cementing solution and water, and mixing well to obtain the improving mixture slurry, where the water is added until the improving mixture slurry is thin enough to be sprayed from a spray pipe by greening wet spraying; the microbial solution and the cementing solution are each added once in the whole process;

(5) with reference to FIGS. 1-2, laying a three-dimensional vegetation net: leveling an excavated slope; constructing an intercepting ditch 1 on a crest of the slope, a drainage ditch 2 on a toe of the slope and a drainage groove 3 on a face of the slope; laying the three-dimensional vegetation net 4 on the face of the slope from top to bottom, and fixing the three-dimensional vegetation net 4, where the three-dimensional vegetation net extends 40-80 cm on the crest of the slope to be buried in the soil and compacted; a longitudinal/transverse tensile strength of the three-dimensional vegetation net is greater than 1.0 kN/m; and (6) spraying and sowing: spraying the improving mixture slurry by wet spraying to the face of the slope twice from top to bottom and left to right with a thickness of 4±1 cm each; then mixing the improving mixture slurry with grass seeds well, and spraying to the face of the slope once, where the spraying thickness is 4±1 cm, and the total thickness of the sprayed improving mixture slurry on the face of the slope is not less than 10 cm; not less than 25 g of grass seeds are sown per square meter of the face of the slope; the prepared improving mixture slurry is sprayed to the face of the slope in 6 h; then covering with a non-woven fabric by tying and fixing, and watering every day.

Advantages of the Present Invention

The construction method is simple. It meets the requirements of greening the expansive soil slope, resisting rain erosion and preventing a shallow landslide. It reduces the stock of solid phosphogypsum waste, thereby reducing the occupation of cultivated land, and promotes plant growth with available phosphorus in the phosphogypsum, turning waste into treasure. The microbial culture uses a cheap medium, which reduces the operation cost. The microbial improvement of the phosphogypsum achieves the immobilization of harmful elements, thereby reducing environmental pollution.

Applications of the Present Invention

Greening protection and rain erosion resistance protection of slopes in highway and railway engineering, etc.

DETAILED DESCRIPTION

Figure 1:
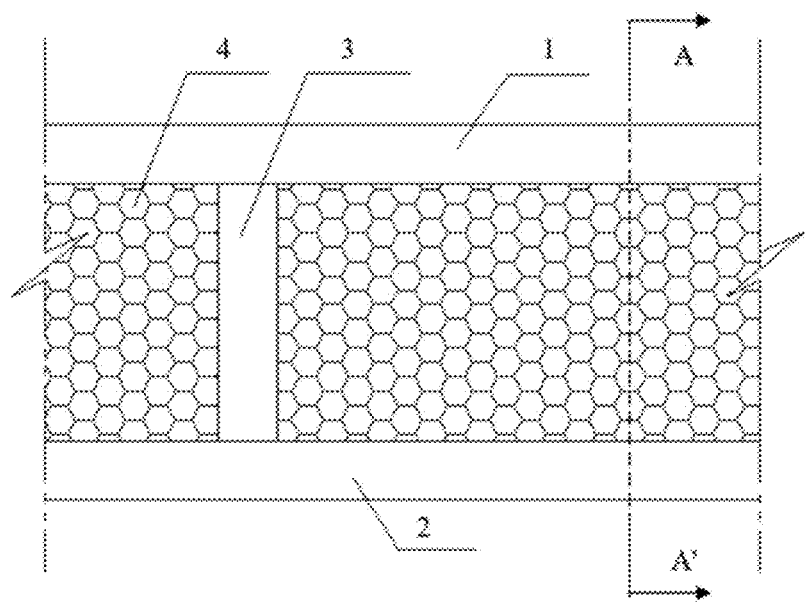
FIG. 1 is a schematic elevation view of a slope paved with a three-dimensional vegetation net, wherein numeral 1 refers to intercepting ditch, numeral 2 refers to drainage ditch, numeral 3 refers to drainage groove and numeral 4 refers to three-dimensional vegetation network.

Example: a construction method for ecologically protecting an expansive soil slope by combining phosphogypsum with microbial mineralization, including the following steps:

(1) Prepare a culture medium and a microbial solution: weigh 8 kg of bean pulp, 2 kg of $(NH_4)_2SO_4$, 0.71 kg of $Na_2HPO_4$ and 8 kg of NaOH to prepare a mixed solute of the culture medium; mix the mixed solute of the culture medium with 200 kg of water to prepare a liquid medium; seal and sterilize the liquid medium in an autoclave at 121° C. for 25 min, and then cool to 30° C. for use; add 2 L of *Bacillus pasteurii* solution to the liquid medium to prepare the microbial solution; place the microbial solution into a constant-temperature shaking incubator at 30° C., and shake at 200 rpm for more than 24 h until an optical density of the *Bacillus pasteurii* in the microbial solution at a wavelength of 600 nm ($OD_{600}$) is 1.5.

(2) Prepare a cementing solution: weigh 240 kg of urea and 120 kg of calcium chloride, mix with water to prepare 2,020 L of cementing solution with a concentration of 0.5 mol.

(3) Prepare a mixture: weigh 43.0 t of phosphogypsum, 2.2 t of alkaline slag and 106.2 t of loam, and mix well to obtain the mixture.

(4) Prepare an improving mixture slurry: mix 101.0 m³ of mixture, 0.2 m³ of microbial solution and 20 m³ of water well; then add 2 m³ of cementing solution and 8 m³ of water, and mix well to obtain the improving mixture slurry, where the mixture has a bulk density of 1.5 g/cm³.

Figure 2:
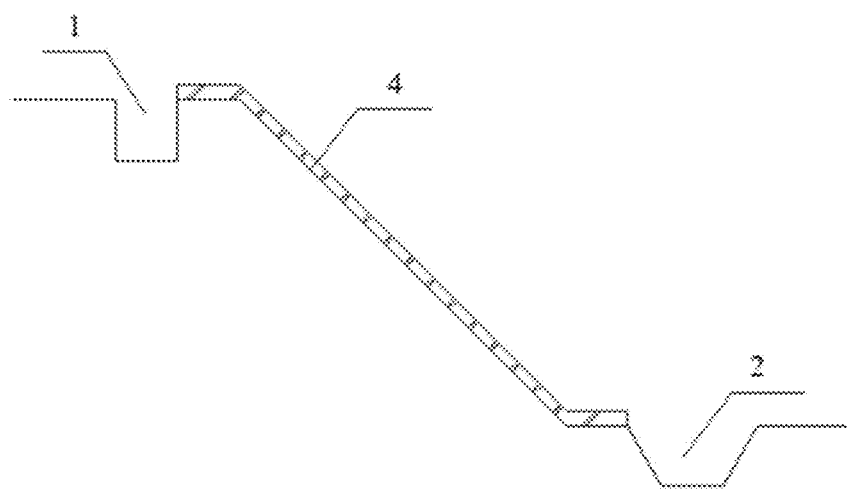
FIG. 2 is a schematic cross-sectional view of AA' in FIG. 1, wherein numeral 1 refers to intercepting ditch, numeral 2 refers to drainage ditch, and numeral 4 refers to three-dimensional vegetation network.

(5) Slope protection: With reference to FIGS. 1-2, level an excavated slope; construct an intercepting ditch 1 on a crest of the slope, a drainage ditch 2 on a toe of the slope and a drainage groove 3 on a face of the slope: lay a three-dimensional vegetation net 4; spray the improving mixture slurry by wet spraying to the face of the slope twice front top to bottom and left to right with a thickness of 4 cm each; then mix the improving mixture slurry with grass seeds well, and spray to the face of the slope once with a thickness of 3 cm; then cover with a non-woven fabric by tying and fixing, and water every day.

What is claimed is:

1. A design and construction method of an expansive sol slope conditioned with phosphogypsum and a microbe, comprising the following steps:

(1) preparing a culture medium and a microbial solution, wherein a mixed solute in the culture medium comprises bean pulp, $(NH_4)_2SO_4$, $Na_2HPO_4$ and NaOH: weighting 40 parts of bean pulp, 10 parts of $(NH_4)_2SO_4$, 3.55 parts of $Na_2HPO_4$ and 40 parts of NaOH by mass to prepare the mixed solute of the culture medium; mixing the mixed solute of the culture medium with water to prepare a liquid medium, the content of the bean pulp in the liquid medium being controlled at 20-60 g/L; sealing and sterilizing the liquid medium in an autoclave at 121° C. for 25 min, and then cooling to 30±2° C. for use; adding 1 part by volume of *Bacillus pasteurii* solution to 100 parts by volume of liquid medium to prepare the microbial solution; placing the microbial solution into a constant-temperature shaking incubator at 30° C., and shaking at 200 rpm for more than 24 h until an optical density of the microbe in the microbial solution at a wavelength of 600 nm ($OD_{600}$) is 1.5±0.2;

(2) preparing a cementing solution, wherein a mixed solute in the cementing solution comprises urea and calcium chloride: weighing 2 parts of granular urea and 1 part of powdered calcium chloride by mass to prepare the mixed solute, and mixing the mixed solute with water to prepare the cementing solution with a concentration of 0.5±0.1 mol;

(3) preparing a mixture comprising phosphogypsum, fly ash and soil: weighing 19 parts of phosphogypsum, 1 part of fly ash and 40-50 parts of sod by dry mass, and mixing well to the mixture, wherein the soil in the mixture is expansive soil, loam or planting soil;

(4) preparing an improving mixture slurry: weighing 100-1,000 pans of mixture, 1 part of microbial solution and 10 parts of cementing solution by volume; first mixing the 100-1,000 parts of mixture and 1 part of microbial solution with water well; then adding the 10 parts of cementing solution and water, and mixing well to obtain the improving mixture slurry, wherein the microbial solution and the cementing solution are each added once in the whole process;

(5) laying a three-dimensional vegetation net: leveling an excavated slope; constructing an intercepting ditch on a crest of the slope, a drainage ditch on a toe of the slope and a drainage groove on a face of the slope; laying the three-dimensional vegetation net on the face of the slope from top to bottom, and fixing the three-dimensional vegetation net, wherein the three-dimensional vegetation net extends 40-80 cm on the crest of the slope to be buried in the soil and compacted; a longitudinal/transverse tensile strength of the three-dimensional vegetation net is greater than 1.0 kN/m; and (6) spraying and sowing: spraying the improving mixture slurry by wet spraying to the face of the slope twice from top to bottom and left to right with a thickness of 4±1 cm each; then mixing the improving mixture slurry with grass seeds well, and spraying to the face of the slope once, wherein the spraying thickness is 4±1 cm, and the total thickness of the sprayed improving mixture slurry on the face of the slope is not less than 10 cm; not less than 25 g of grass seeds are sown per square meter of the face of the slope; the prepared improving mixture slurry is sprayed to the face of the slope in 6 h; then covering with a non-woven fabric by tying and fixing to the slope, and watering every day.

\* \* \* \* \*